(12) United States Patent
Yang et al.

(10) Patent No.: US 12,364,682 B2
(45) Date of Patent: Jul. 22, 2025

(54) USE OF TEGASEROD IN PREPARATION OF ANTI-TUMOR DRUG

(71) Applicants: Qingdao Haiji Biomedicine Co., Ltd., Shandong (CN); MARINE BIOMEDICAL RESEARCH INSTITUTE OF QINGDAO CO., LTD., Shandong (CN)

(72) Inventors: Jinbo Yang, Shandong (CN); Qiaoling Song, Shandong (CN); Chenyang Zhao, Shandong (CN); Lijuan Wu, Shandong (CN); Jun Zhao, Shandong (CN); Dan Yao, Shandong (CN); Yu Tang, Shandong (CN); Ximing Xu, Shandong (CN); Menglin Yang, Shandong (CN)

(73) Assignees: Qingdao Haiji Biomedicine Co., Ltd., Shandong (CN); MARINE BIOMEDICAL RESEARCH INSTITUTE OF QINGDAO CO., LTD., Shandong (CN)

( * ) Notice: Subject to any disclaimer, the term of this patent is extended or adjusted under 35 U.S.C. 154(b) by 844 days.

(21) Appl. No.: 17/604,795

(22) PCT Filed: Apr. 17, 2020

(86) PCT No.: PCT/CN2020/085382
§ 371 (c)(1),
(2) Date: Jan. 11, 2022

(87) PCT Pub. No.: WO2020/211847
PCT Pub. Date: Oct. 22, 2020

(65) Prior Publication Data
US 2022/0218666 A1    Jul. 14, 2022

(30) Foreign Application Priority Data

Apr. 19, 2019  (CN) .......................... 201910318535.6

(51) Int. Cl.
| A61K 31/4045 | (2006.01) |
| A61K 9/00 | (2006.01) |
| A61P 35/00 | (2006.01) |

(52) U.S. Cl.
CPC ........ *A61K 31/4045* (2013.01); *A61K 9/0019* (2013.01); *A61K 9/0053* (2013.01); *A61P 35/00* (2018.01)

(58) Field of Classification Search
CPC .............. A61K 31/4045; A61K 9/0019; A61K 9/0053; A61P 35/00
See application file for complete search history.

(56) References Cited

U.S. PATENT DOCUMENTS 11,034,751 B1 *  6/2021  Kahvejian .......... C07K 14/5421
2020/0325543 A1 * 10/2020  Flückiger-Mangual ..................... C12Q 1/6886

OTHER PUBLICATIONS

Varbanov, Hristo P., Fabien Kuttler, Damiano Banfi, Gerardo Turcatti, and Paul J. Dyson. "Repositioning approved drugs for the treatment of problematic cancers using a screening approach." PloS one 12, No. 2 (2017): e0171052. (Year: 2017).*
S5 from Supporting Info for Varbanov et al (see ref) (Year: 2017).*
S1, Table 1 from Supporting Info for Varbanov et al (see ref) (Year: 2017).*
Johnson, J. I., S. Decker, D. Zaharevitz, L. V. Rubinstein, J. M. Venditti, S. Schepartz, S. Kalyandrug et al. "Relationships between drug activity in NCI preclinical in vitro and in vivo models and early clinical trials." British journal of cancer 84, No. 10 (2001): 1424-1431 (Year: 2001).*

* cited by examiner

*Primary Examiner* — James H Alstrum-Acevedo
*Assistant Examiner* — Carolyn L. Ladd
(74) *Attorney, Agent, or Firm* — Harness, Dickey & Pierce, P.L.C.

(57) ABSTRACT

The present disclosure discloses the use of Tegaserod or a pharmaceutically acceptable salt thereof as a JAK-STAT3 signaling pathway inhibitor and an immunomodulator in the preparation of an anti-tumor drug. Tegaserod and the pharmaceutically acceptable salt thereof show a very excellent inhibitory effect on the growth of various tumor cells in vivo and in vitro, and are expected to be used in the treatment of various cancers.

9 Claims, 8 Drawing Sheets

USE OF TEGASEROD IN PREPARATION OF ANTI-TUMOR DRUG

CROSS-REFERENCE TO RELATED APPLICATIONS

This application is a 371 U.S. National Phase of International Application No. PCT/CN2020/085382 filed on Apr. 17, 2020, which claims the benefit and priority of Chinese Patent Application No. 201910318535.6, filed on Apr. 19, 2019. The entire disclosures of the above applications are incorporated herein by reference.

TECHNICAL FIELD

The present disclosure belongs to the field of medical applications, and relates to a novel medical use of Tegaserod. Specifically, as a JAK-STAT3 signaling pathway inhibitor and an immunomodulator, Tegaserod can be used to prepare an anti-tumor drug.

BACKGROUND ART

Tumor is currently on the top of the diseases threatening the human health and life, and current clinical drugs are far from meeting the needs of patients. Therefore, the development of anti-tumor drugs is an extremely important research direction in the field of drug research and development at present.

JAK-STAT signals in cells are essential for cell signaling and various physiological activities. Abnormal signals in this family can lead to the occurrence of many diseases, including cancer and immune-related diseases. The JAK family includes four members, that is, JAK1, JAK2, JAK3, and Tyk2. The STAT family, downstream of JAK, includes 7 members, of which STAT3 is an important family member, which is constitutively activated by abnormal upstream tyrosine kinases (TKs) in many tumor cell lines and human tumors. Abnormal STAT3 signals participate in the occurrence and development of human tumors by stimulating cell proliferation, promoting angiogenesis, and inhibiting cell apoptosis. Therefore, inhibiting the JAK-STAT3 signaling pathway is a potentially feasible clinical treatment strategy for tumors.

At present, clinical treatment strategies by inhibiting the JAK-STAT3 signaling pathway mainly include: 1. using tyrosine kinase inhibitors (TKIs) targeting upstream STAT3 signaling molecules, including JAK kinase family inhibitors, 2. blocking the STAT3 gene expression or protein function, such as dominant-negative STAT protein or RNAi interference for STAT3, and 3. taking advantage of small molecules to inhibit the STAT3 activation and dimerization.

In recent years, with the rapid increase in the development cost of new drugs and the gradual decline in the success rate of drug development, new drugs fail to fill the gap resulting from the expiration of most drug patents. Under these circumstances, pharmaceutical companies have tried to develop new patented drugs on the basis of existing drugs. "New use of old drugs" has become a hot spot in international drug research and development.

Tegaserod (formula I), with a chemical name of 2-[(5-methoxy-1H-indol-3-yl)methylene]-N-pentylcarbazide, is a selective 5-hydroxytryptamine 4 (5-HT4) receptor agonist, and a maleate thereof was approved by the Food and Drug Administration (FDA) in 2002 for the treatment of irritable bowel syndrome (IBS). In addition, Tegaserod shows a therapeutic effect on a variety of gastrointestinal disorders, including such as pyrosis, aerogastria, postoperative ileus, abdominal pain and discomfort, epigastric pain, nausea, vomiting, intestinal pseudo-obstruction, and gastroesophageal reflux.

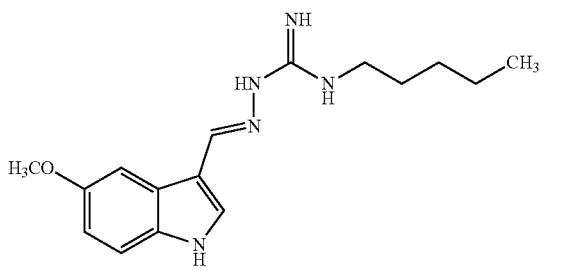

(I)

SUMMARY

The present disclosure unexpectedly found that Tegaserod can inhibit the activity of JAK-STAT3 signaling pathway, suppress the tumor growth, and activate the peripheral immune response and the immune response in tumor microenvironment (TME), which shows an anti-tumor effect on various tumors in vivo and in vitro.

Based on the above findings, the present disclosure provides the use of Tegaserod or a pharmaceutically acceptable salt thereof in the preparation of an anti-tumor drug.

In a preferred embodiment of the present disclosure, the tumor may involve abnormal activation of the JAK-STAT3 signaling pathway.

In a more preferred embodiment of the present disclosure, the abnormal activation of the JAK-STAT3 signaling pathway may be manifested as an increased phosphorylation level of JAK1, JAK2, JAK3, Tyk2, or STAT3, and preferably, the increased phosphorylation level may refer to an increased phosphorylation level at a site JAK1 Tyr1022/1023, JAK2 Tyr1007/1008, TYK2 Tyr1054/1055, or STAT3 Tyr705.

In a preferred embodiment of the present disclosure, the anti-tumor drug can activate and/or enhance an immune response.

In a more preferred embodiment of the present disclosure, the immune response may refer to a mammalian immune response.

In a more preferred embodiment of the present disclosure, the immune response may include a peripheral immune response and/or an immune response in TME; more preferably, activating and/or enhancing a peripheral immune response may include: increasing the number of each of white blood cells (WBCs), neutrophils, lymphocytes, and platelets in the peripheral blood; and activating and/or enhancing the anti-tumor immune response in TME may include: increasing infiltration of immune cells (CD45+) within a tumor, and partially or completely increasing a proportion of one or more from the group consisting of killer T cells (CD8+), helper T cells (CD4+), activated T cells (CD4+CD69+ and CD8+CD69+), tumor-infiltrating inflammatory neutrophils (CD11b+Ly6G+), monocytes/macrophages (CD11b+Ly6C+), and natural killer cells (CD335+).

In a preferred embodiment of the present disclosure, the pharmaceutically acceptable salt may be Tegaserod maleate.

In a preferred embodiment of the present disclosure, the tumor may be selected from the group consisting of cerebroma, genitourinary system tumor, lymphatic system tumor, gastric cancer, laryngeal cancer, nasopharyngeal cancer, skin cancer, bone cancer, blood cancer, leukemia, breast cancer, histiocytic lymphoma, non-small cell lung cancer (NSCLC), small cell lung cancer (SCLC), lung adenocarcinoma, lung squamous cell carcinoma, pancreatic cancer, prostate cancer, cervical cancer, liver cancer, skin carcinoma, and epithelial cell cancer; and preferably, the tumor may be selected from the group consisting of prostate cancer, lung cancer, and colon cancer.

In addition, the Tegaserod or the pharmaceutically acceptable salt thereof can also be used in combination with an anti-tumor drug currently in use or under development to increase the clinical effect.

The Tegaserod and the pharmaceutically acceptable salt thereof show a very excellent inhibitory effect on the growth of various tumor cells in vivo and in vitro, and are expected to be used in the treatment of various cancers. The present disclosure provides a new therapeutic candidate drug for tumor patients, which may further improve the therapeutic effect on the patients and improve the prognosis for the patients.

DETAILED DESCRIPTION

Figure 1:
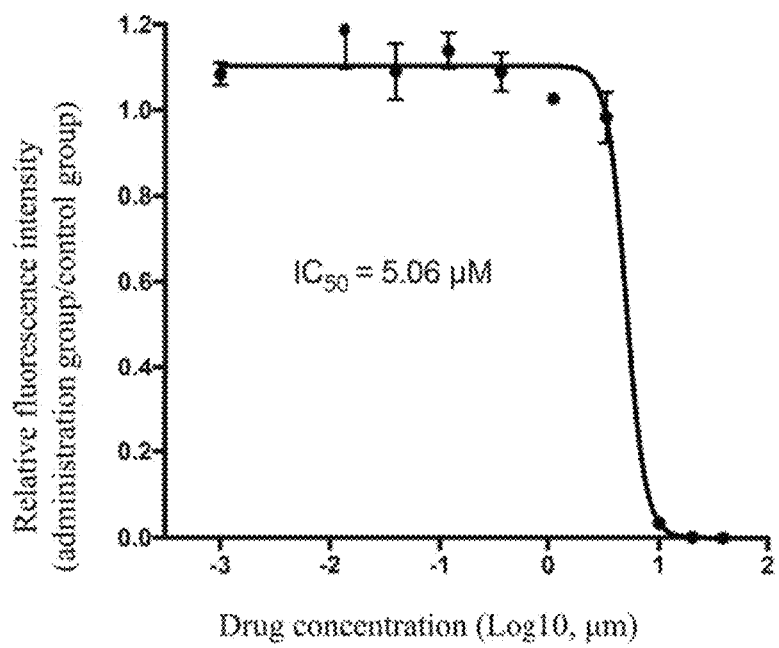
FIG. 1 shows an inhibitory effect of Tegaserod maleate on the expression of a reporter gene in an STAT3 luciferase drug screening system.

The present disclosure provides the use of Tegaserod, and a free form, a pharmaceutically acceptable salt, a prodrug, and an active metabolite thereof in the preparation of an anti-tumor drug.

The free form of a particular Tegaserod salt can be isolated using techniques known in the art. For example, the Tegaserod salt can be treated with a suitable dilute aqueous solution of an alkali (such as a dilute aqueous solution of NaOH, a dilute aqueous solution of potassium carbonate, a dilute ammonia solution, and a dilute aqueous solution of sodium bicarbonate) to regenerate the free form. The free form is somewhat different from the corresponding salt form in some physical properties such as solubility in polar solvents, but for the purpose of the present disclosure, such acid and base salts are equivalent to the respective free forms in other pharmaceutical aspects.

The pharmaceutically acceptable salt of the present disclosure can be synthesized from Tegaserod by conventional chemical methods. Generally, it is prepared by ion exchange chromatography or by subjecting a free alkali and a stoichiometric amount or an excess amount of an inorganic or organic acid for a desired salt form to a reaction in a suitable solvent or a combination of multiple solvents. Therefore, the pharmaceutically acceptable salt of Tegaserod of the present disclosure includes a conventional non-toxic salt of the compound of the present disclosure formed by subjecting Tegaserod and an inorganic or organic acid to a reaction. For example, the conventional non-toxic salt may include a salt derived from an inorganic acid such as hydrochloric acid, hydrobromic acid, sulfuric acid, sulfamic acid, phosphoric acid, and nitric acid; and a salt derived from an organic acid such as acetic acid, propionic acid, succinic acid, glycolic acid, stearic acid, lactic acid, malic acid, tartaric acid, citric acid, ascorbic acid, pamoic acid, maleic acid, hydroxymaleic acid, phenylacetic acid, glutamic acid, benzoic acid, salicylic acid, sulfanilic acid, 2-acetoxybenzoic acid, fumaric acid, toluenesulfonic acid, methanesulfonic acid, ethanedisulfonic acid, oxalic acid, isethionic acid, and trifluoroacetic acid. The conventional non-toxic salt may preferably be a maleate.

The present disclosure relates to the use of Tegaserod or a pharmaceutically acceptable salt thereof as a small-molecule inhibitor of JAK-STAT3 signaling pathway in the preparation of an anti-tumor drug.

In an embodiment, the present disclosure provides the use of Tegaserod or the pharmaceutically acceptable salt thereof in treating hyperproliferative diseases or symptoms such as human or other mammalian tumors.

In an embodiment, the compound and the pharmaceutically acceptable salt thereof involved in the present disclosure can be used to treat or control histiocytic lymphoma, NSCLC, SCLC, lung adenocarcinoma, lung squamous cell carcinoma, pancreatic cancer, breast cancer, prostate cancer, liver cancer, skin cancer, epithelial cell cancer, prostatic carcinoma, nasopharyngeal cancer, epidermal cell carcinoma, cervical cancer, oral cancer, human fibrosarcoma, leukemia, and other hyperproliferative diseases.

The Tegaserod or the pharmaceutically acceptable salt thereof involved in the present disclosure can be used to treat the following diseases and other diseases not listed below according to the following methods:

1) A method for treating breast cancer in humans or other mammals using a pharmaceutical composition of the Tegaserod or the pharmaceutically acceptable salt thereof. The breast cancer includes, but is not limited to, invasive ductal carcinoma, invasive lobular carcinoma, ductal carcinoma in situ (DCIS), and lobular carcinoma in situ (LCIS).

2) A method for treating respiratory cancer in humans or other mammals using a pharmaceutical composition of the Tegaserod or the pharmaceutically acceptable salt thereof. The respiratory cancer includes, but is not limited to, SCLC, NSCLC, bronchial adenoma, and pleuropulmonary blastoma (PPB).

3) A method for treating brain cancer in humans or other mammals using a pharmaceutical composition of the Tegaserod or the pharmaceutically acceptable salt thereof. The brain cancer includes, but is not limited to, brain stem and subocular gliomas, cerebellar and cerebral astrocytomas, ependymomas, and neuroectodermal and pineal tumors.

4) A method for treating tumors in male and female reproductive organs of humans or other mammals using a pharmaceutical composition of the Tegaserod or the pharmaceutically acceptable salt thereof. The tumors in the male reproductive organs include, but are not limited to, prostate cancer and testicular cancer. The tumors in the female reproductive organs include, but are not limited to, endometrial cancer, cervical cancer, ovarian cancer, vaginal cancer, vulvar cancer, and intrauterine tumor.

5) A method for treating tumors in digestive tracts of humans or other mammals using a pharmaceutical composition of the Tegaserod or the pharmaceutically acceptable salt thereof. The tumors in digestive tracts include, but are not limited to, anal cancer, colon cancer, colorectal cancer (CRC), esophageal cancer, gastric cancer, pancreatic cancer, rectal cancer, small intestine cancer, and salivary gland cancer.

6) A method for treating tumors in urethrae of humans or other mammals using a pharmaceutical composition of the Tegaserod or the pharmaceutically acceptable salt thereof. The tumors in the urethrae include, but are not limited to, bladder cancer, penile cancer, kidney cancer, renal pelvis cancer, ureter cancer, and urethral cancer.

7) A method for treating eye cancer in humans or other mammals using a pharmaceutical composition of the Tegaserod or the pharmaceutically acceptable salt thereof. The eye cancer includes, but is not limited to, intraocular melanoma and retinocytoma.

8) A method for treating liver cancer in humans or other mammals using a pharmaceutical composition of the Tegaserod or the pharmaceutically acceptable salt thereof. The liver cancer includes, but is not limited to, hepatocellular carcinoma (HCC) (with or without fibrolamellar changes), cholangiocarcinoma (intrahepatic cholangiocarcinoma (ICC)), and mixed hepatocellular cholangiocarcinoma.

9) A method for treating skin cancer in humans or other mammals using a pharmaceutical composition of the Tegaserod or the pharmaceutically acceptable salt thereof. The skin cancer includes, but is not limited to, squamous cell carcinoma, Kaposi's sarcoma, malignant melanoma, Merkel cell skin cancer, and non-melanoma skin cancer.

10) A method for treating head and neck cancer in humans or other mammals using a pharmaceutical composition of the Tegaserod or the pharmaceutically acceptable salt thereof. The head and neck cancer includes, but is not limited to, laryngeal cancer, hypopharyngeal cancer, nasopharyngeal cancer, oropharyngeal cancer, lip cancer, and oral cancer.

11) A method for treating lymphoma in humans or other mammals using a pharmaceutical composition of the Tegaserod or the pharmaceutically acceptable salt thereof. The lymphoma includes, but is not limited to, AIDS-related lymphoma, non-Hodgkin's lymphoma (NHL), cutaneous T cell lymphoma (CTCL), Hodgkin's disease, and central nervous system lymphoma (CNSL).

12) A method for treating sarcoma in humans or other mammals using a pharmaceutical composition of the Tegaserod or the pharmaceutically acceptable salt thereof. The sarcoma includes, but is not limited to, soft tissue sarcoma (STS), osteosarcoma, malignant fibrous histiocytoma (MFH), lymphosarcoma, and rhabdomyosarcoma (RMS).

13) A method for treating leukemia in humans or other mammals using a pharmaceutical composition of the Tegaserod or the pharmaceutically acceptable salt thereof. The leukemia includes, but is not limited to, acute myeloid leukemia (AML), acute lymphoblastic leukemia (ALL), chronic lymphocytic leukemia (CLL), chronic myeloid leukemia (CML), and hairy cell leukemia (HCL).

According to standard pharmaceutical techniques, Tegaserod or the pharmaceutically acceptable salt thereof of the present disclosure can be administered to mammals (preferably humans) alone or in combination with a pharmaceutically acceptable receptor, an adjuvant, or a diluent (as a pharmaceutical composition). Tegaserod or the pharmaceutically acceptable salt thereof of the present disclosure can be administered orally, subcutaneously, intramuscularly, intraperitoneally, intravenously, rectally, topically, ocularly, pulmonarily, nasally, or parenterally.

Active metabolites of Tegaserod or the pharmaceutically acceptable salt thereof involved in the present disclosure, and prodrugs that can be converted in vivo into the structure of the compound or the pharmaceutically acceptable salt thereof involved in the present disclosure are also included in the claims of the present disclosure.

The term "immune response" refers to a defense and recognition response of the body to foreign components or variational autologous components. According to an occurrence or action site of an immune response in the body, the immune response usually includes a systemic immune response and a local immune response.

The term "peripheral immune response" refers to a systemic immune response, which involves the extensive activation of an immune system at a site far away from a tumor and includes: activation, phenotypic change, proliferation, or the like of immune cells circulating in blood caused by foreign or variational autologous components or danger associated molecular patterns (DAMPs) released by autologous cells; and immune responses in lymph nodule, spleen or intestine-related lymphoid tissues.

The TME is composed of tumor cells and infiltrating immune cells, new blood vessels and endothelial cells thereof, tumor-associated fibroblasts, and extracellular matrix (ECM) around a tumor, which can promote the tumor progression, increase the tumor invasiveness, evade the host immunity, and fight against the treatment response. The term "immune response in TME" refers to a local immune response, which usually includes the composition, activity, and function of immune cells in TME. In the present disclosure, the immune response in TME may include the change of proportions of immune cells within a tumor (CD45+), killer T cells (CD8+), helper T cells (CD4+), activated T cells (CD4+CD69+ and CD8+CD69+), tumor-infiltrating inflammatory neutrophils (CD11b+Ly6G+), monocytes/macrophages (CDIIb+Ly6C+), natural killer cells (CD335+), and the like. Activating and/or enhancing the immune response in TME refers to increasing the number or proportion of all or some of the above-mentioned cells.

Tegaserod can be used in combination with other known drugs to treat or improve similar conditions. In the case of combined administration, the original drug is administered according to the original route and dosage, and Tegaserod is administered simultaneously with or subsequently of the original drug. When Tegaserod and one or more other drugs are administered at the same time, it is preferable to use a pharmaceutical composition including the one or more known drugs and Tegaserod. The combined administration also includes administering Tegaserod and one or more other known drugs in overlapping time periods. When Tegaserod is used in combination with one or more other drugs, a dosage of Tegaserod or a known drug may be lower than a dosage at which the Tegaserod or the known drug is used alone.

Drugs or active ingredients that can be used in combination with Tegaserod to treat tumors include, but are not limited to:

an estrogen receptor modulator, an androgen receptor modulator, a retinoid receptor modulator, a cytotoxin/cytostatic agent, an antiproliferative agent, a protein transferase inhibitor, an HMG-CoA reductase inhibitor, an HIV protein kinase inhibitor, a reverse transcriptase inhibitor, an angiogenesis inhibitor, a cell proliferation and survival signal inhibitor, a drug for interfering with cell cycle checkpoints, an apoptosis inducer, a cytotoxic drug, a tyrosine protein inhibitor, an EGFR inhibitor, a VEGFR inhibitor, a serine/threonine protein inhibitor, a Bcr-Abl inhibitor, a c-Kit inhibitor, a Met inhibitor, a Raf inhibitor, an MEK inhibitor, an MMP inhibitor, a topoisomerase inhibitor, a histone deacetylase inhibitor, a proteasome inhibitor, a CDK inhibitor, a Bcl-2 family protein inhibitor, a MDM2 family protein inhibitor, an IAP family protein inhibitor, an STAT family protein inhibitor, a PI3K inhibitor, an AKT inhibitor, an integrin blocker, interferon-α, interleukin-12, a COX-2 inhibitor, a p53 activator, a p53 activator, a VEGF antibody, and an EGF antibody.

In an embodiment, drugs or active ingredients that can be used in combination with Tegaserod to treat tumors include, but are not limited to: aldesleukin, alendronic acid, alfaferone, alitretinoin, allopurinol, aloprim, aloxi, altretamine, aminoglutethimide, amifostine, amrubicin, amsacrine, anastrozole, anzmet, aranesp, arglabin, arsenic trioxide, aromasin, 5-azacytidine, azathioprine, Bacille Calmette-Guerin (BCG) or tice BCG, bestatin, betamethasone acetate, betamethasone sodium phosphate, bexarotene, bleomycin sulfate, bromouridine, bortezomib, busulfanum, calcitonin, campath, capecitabine, carboplatin, casodex, cefesone, celmoleukin, daunorubicin, chlorambucil, cisplatin, cladribine, cladribine, clodronate, cyclophosphamide, cytarabine, dacarbazine, actinomycin D, liposomal daunorubicin, dexamethasone, dexamethasone phosphate, estradiol valerate, denileukin diftitox 2, methylprednisolone, deslorelin, dexrazoxane, diethylstilbestrol, diflucan, docetaxel, doxifluridine, doxorobicin, dronabinol, holmium-166-chitosan complex, eligard, eliteck, ellence, emend, epirubicin, epoetin-alfa, epogen, eptaplatin, ergamisole, estrace, 17-β-estradiol, estramustine sodium phosphate, ethinyloestradiol, ethyol, etidronic acid, etopophos, etoposide, fadrozole, farstone, filgrastim, finasteride, fligrastim, floxuridine, fluconazole, fludarabine, 5-fluorodeoxyuridine monophosphate, 5-fluorouracil, fluoxymesterone, flutamide, formestane, fosteabine, fotemustine, fulvestrant, gamma globulin, gemcitabine, gemtuzumab, gleevec, gliadel, goserelin, granisetron hydrochloride, histrelin, hycamtin, hydrocortisone, erythrohydroxynonyl adenine, hydroxyurea, ibritumomab tiuxetan, idarubicin, ifosfamide, interferon α, interferon-α2, interferon α-2A, interferon α-2B, interferon α-n1, interferon α-n3, interferon β, interferon γ-1a, interleukin-2, intron A, iressa, irinotecan, kytril, lentinan sulfate, letrozole, leucovorin, leuprorelin, leuprorelin acetate, levotetramisole, levoleucovorin calcium, levothyroxine sodium, levothyroxine sodium preparation, lomustine, lonidamine, marinol, mechlorethamine, methylcobalamin, medroxyprogesterone acetate, megestrol acetate, melphalan, menest, 6-mercaptopurine, mesna, methotrexate, methyl aminolevulinate, miltefosine, minocycline, mitomycin C, mitotane, mitoxantrone, modrenal, myocet, nedaplatin, neulasta, neumega, neupogen, nilutamide, nolvadex, NSC-631570, recombinant human interleukin 1-β, octreotide, ondansetron hydrochloride, oraprep, oxaliplatin, paclitaxel, pediapred, pegaspargase, pegasys, pentostatin, picibanil, pilocarpine hydrochloride, pirarubicin, plicamycin, porfimer sodium, prednimustine, prednisolone steaglate, prednisone, premarin, procarbazine, procrit, raltitrexed, rebif, rhenium-186 etidronate, rituxan, redoxon-A, romurtide, salagen, sandostatin, sargramostim, semustine, sizofiran, sobuzoxane, solu-medrol, sparfosic acid, stem cell therapy, streptozocin, strontium-89 chloride, synthroid, tamoxifen, tamsulosin, tasonamin, tastolactone, taxotere, teceleukin, temozolomide, teniposide, testosterone propionate, testride, thioguanine, thiotepa, thyrotropin, tiludronic acid, topotecan, toremifene, tositumomab, trastuzumab, treosulfan, tretinoin, trexall, trimethylmelamine, trimetrexate, triptorelin acetate, triptorelin pamoate, UFT, uridine, valrubicin, vesnarinone, vinblastine, vincristine, vindesine, vinorelbine, virulizin, zinecard, zinostatin stimalamer, zofran, ABI-007, acolbifene, actimmune, affinitak, aminopterin, arzoxifene, asoprisnil, atamestane, atrasentan, BAY43-9006, avastin, CCI-779, CDC-501, celebrex, cetuximab, crisnatol, cyprottreone acetate, decitabine, DN-101, doxorubicin-MTC, dSLIM, dutasteride, edotecarin, eflornithine, exatecan, fenretinide, histamine dihydrochloride, histrelin hydrogel implant, holmium-166 DOTMP, ibandronic acid, interferon γ, intron-PEG, ixabepilone, keyhole limpet hemocyanin, L-651582, lanreotide, lasofoxifene, libra, lonafamib, miproxifene, minodronate, MS-209, liposomal MTP-PE, MX-6, nafarelin, nemorubicin, neovastat, nolatrexed, oblimersen, onco-TCS, osidem, polyglutamate paclitaxel, pamidronate disodium, PN-401, QS-21, quazepam, R-1549, raloxifene, ranpirnase, 13-cis retinoic acid, satraplatin, seocalcitol, T-138067, tarceva, taxoprexin, thymosin α1, tiazofurin, tipifarnib, tirapazamine, TLK-286, toremifene, trans-MID-lo7R, valspodar, vapreotide, vatalanib, verteporfin, vinflunine, Z-100, and zoledronic acid, or a combination thereof.

The present disclosure will be further described below in conjunction with specific examples. The examples are provided to help further understand the present disclosure, and the specific materials, methods, and the like used therein are for describing the present disclosure, and do not constitute a limitation on the scope of the present disclosure.

The experimental materials and general experimental methods used in the examples are as follows, which are used according to instructions of manufacturers unless otherwise specified.

1. Antibodies and Reagents

The p-Tyr705-STAT3, p-Tyr1022/1023-JAK1, p-Tyr1007/1008-JAK2, and p-Tyr1054/1055-Tyk2 antibodies were purchased from Cell Signaling Technology®, and the α-Tubulin antibody was purchased from Santa Cruz®. The recombinant human IL-6 cytokine was purchased from Peprotech®. The CD11b-PE-Cyanine 7, CD8a-PerCP-eFluor™ 710, CD45-APC-eFluor 780, Rat IgG1 kappa Isotype Control (eBRG1), and Anti-Mo CD32/CD16 antibodies were purchased from Invitrogen®. The CD11b-AF488, CD4-Brilliant Violet 510™, CD206-PE-Cyanine 7, and CD69-PE antibodies were purchased from Biolegend®. The Ly-6G-FITC and Ly-6C-APC antibodies, red blood cell (RBC) lysis buffer, mouse tumor dissociation kit, and human tumor dissociation kit were purchased from Miltenyi Biotec®. The Fixable Viability Dye (eFluor™ 506) and the Ki67 antibody were purchased from BD. The IDEXX® Procyte Dx® Reagent kit and ProCyte Dx® Stain Pack were purchased from an IDEXX® small animal Company. The p-Tyr705-STAT3 antibody was purchased from Cell Signaling Technology. The Matrigel matrix was purchased from Corning.

2. Cell Cultivation

HeLa and SKA cells (A549 cells constructed with the STAT3-luciferase reporter gene) were cultivated in a DMEM medium, and DU145, A549, DLD1, H460, and MC38 were cultivated in an RPMI 1640 medium. For routine cultivation, 10% fetal bovine serum (FBS), 100 IU/ml penicillin, and 100 mg/ml streptomycin were added to a medium. All cells were cultivated at 37° C. and 5% $CO_2$.

3. STAT3-Dependent Luciferase Reporter Gene Test

SKA cells were inoculated into a white 96-well plate at a density of $1\times10^4$/well, and cultivated overnight at 37° C. and 5% $CO_2$. A drug to be tested was added at a concentration to be tested to act on the cells for 24 h. The luciferase activity was determined on a SpectraMax®L microplate reader using a luciferase kit (purchased from Promega®).

4. Western Blotting

The cells were harvested and lysed with an RIPA buffer, a resulting lysate was subjected to sodium dodecyl sulfate-polyacrylamide gel electrophoresis (SDS-PAGE), and a resulting protein was transferred to a nitrocellulose (NC) membrane (purchased from GE Healthcare®). A primary antibody was added to bind the protein to be tested on the membrane, then a horseradish peroxidase (HRP)-conjugated secondary antibody (purchased from Absin) was added for incubation, and finally a formed immunocomplex was detected with an Immobilon™ Western chemiluminescent HRP substrate (Millipore®) and photographed with a Tanon® 5200 imaging system.

5. Flow Cytometry (FCM) Analysis of Tumor Cell Cycle

DU145 cells were inoculated into a 6-well plate at a density of $5\times10^5$/well, and different concentrations of a drug to be tested were added as required or a serum-free medium was used instead. For cell cycle assay, cells were harvested 24 h after treatment, and stained with a cell cycle staining kit (purchased from Lianke Bio., Item No. CCS012); and for apoptosis assay, cells were harvested 48 h after treatment, and stained with an eBioscience™ Annexin V-FITC apoptosis kit (purchased from Invitrogen). Finally, stained cells were tested by FCM.

6. Cell Viability Assay

Cells were inoculated into a 96-well plate at a density of 3,000 cells/well. After the cells were cultivated for 18 h, different concentrations of a drug to be tested were added to act on the cells. 72 h after the drug to be tested was added, 10 µl of resazurin (1 mg/ml) was added to each well, the plate was further incubated for 3 h, and then a fluorescence value at 595 nm (excitation wavelength at 544 nm) was determined on a SpectraMax®i3 multifunctional microplate reader (purchased from Molecular Device®)

7. Transplanted Tumor Animal Model of Nude Mice and Anti-Tumor Activity Assay of Drugs Female NRMI nu/nu athymic nude mice (SPF grade, 6 weeks old, with a weight of 17 g to 20 g) were purchased from GemPharmatech®, and raised in a constant-temperature and constant-humidity environment according to standard requirements, where a 12 h light-dark cycle was adopted. The animal experiment was approved by the Laboratory Animal Committee of Ocean University of China and complied with the "Guide for Care and Use of Laboratory Animals" published by the National Institutes of Health (NIH Publication No. 85-23, revised in 1996).

Nude mice were subcutaneously injected with an A549 cell suspension (female mice) or a DU145 matrigel cell suspension (male mice). After palpable solid tumors were formed, constructed model mice were randomly divided into groups, each with 7 to 10 mice. Administration treatment was conducted according to the experimental grouping. Throughout the experiment, a body weight was measured regularly. A tumor volume was calculated as follows: tumor volume=0.5×length×width×width.

8. FCM Analysis of Immune Cell Surface Markers

At the end of the experiment, the mice were sacrificed by C02, a proper amount of tumor tissue was collected and placed in a dissociation tube with a mouse tumor dissociation reagent (MC38 transplanted tumor) or human tumor dissociation reagent (DU145 transplanted tumor), and a tissue dissociator (Miltenyi) was used for dissociation. Separated single cells were subjected to RBC lysis and dead cell staining, obtained cells were incubated with a blocking solution at 4° C., a corresponding antibody was added, and analysis was conducted on a FACSAriaIII cell sorter.

9. Blood Cell Analysis

After the tumor-bearing mice were sacrificed by $CO_2$, blood was collected from the heart and placed into an EDTA anticoagulation tube, and the blood cell component test was conducted using an IDEXX ProCyte Dx automatic blood cell analyzer.

10. Immunohistochemistry

Paraffin sections were deparaffinized with xylene, washed with ethanol of various grades, subjected to antigen retrieval, blocked with a blocking solution in a 37° C. incubator, then treated with a primary antibody and a secondary antibody, stained with a DAB staining solution, treated with hematoxylin, a differentiation solution, an ammonia solution, ethanol of various grades, and xylene, and sealed with a neutral resin.

11. Transcriptome Sequencing

An appropriate amount of tumor tissue was collected and quick-frozen with liquid nitrogen, and eukaryotic mRNA sequencing was conducted by Majorbio. Based on the Illumina® Novaseq 6000™ sequencing platform, all mRNAs transcribed from specific eukaryotic tissues or cells in a specified period were sequenced. In the sequencing experiment, the Illumina Truseq™ RNA sample prep kit method was used to build a library. Raw data were used for quality control, sequence alignment, transcript assembly, function annotation, and expression analysis. The DESeq2 difference analysis software was used to analyze significantly different genes (p<0.05), and the KEGG signaling pathway analysis was conducted for the significantly different genes.

Example 1 Tegaserod Exhibited Inhibitory Activity in Constitutive STAT3 Activation-Based Luciferase Cell Models Through luciferase-expressing cell models based on constitutive STAT3 activation (see Chinese Patent 1407357), it was found that Tegaserod maleate exhibited a significant inhibitory effect on STAT3 with an $IC_{50}$ of 5.06 µM (FIG. 1).

Example 2 Tegaserod Inhibited the Activation of STAT3

Different concentrations of Tegaserod were added to normally-cultured cells to act on the cells for 2 h, a cell protein lysate was collected for western blotting assay, and an activation status of STAT3 was observed through a phosphorylation status at an STAT3 Tyr705 site.

Results showed that, in DU145 (FIG. 2A) and A549 (FIG. 2B) cells where STAT3 was constitutively activated, Tegaserod could inhibit the activation of STAT3 in a dosage-dependent manner 2 h after drug treatment.

Figure 2:
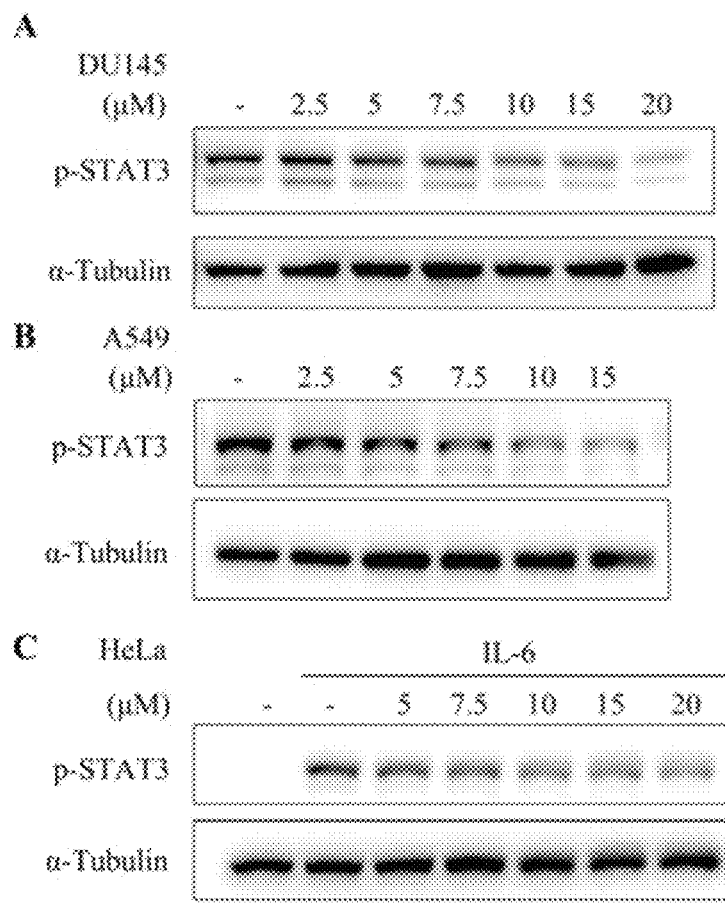
FIG. 2 is a schematic diagram of western blotting results illustrating that Tegaserod can inhibit constitutive activation and IL-6-induced activation of STAT3.

IL-6 was the main cytokine to activate STAT3 signaling. Hela cells were first treated with different concentrations of Tegaserod for 2 h, then stimulated with 5 ng/ml IL-6 for 10 min before harvested. Total protein was extracted, and the phosphorylation of STAT3 (Y705) was detected through western blotting. As shown in FIG. 2C, in HeLa cells, Tegaserod also inhibited the activation of STAT3 induced by IL-6 in a dosage-dependent manner.

Example 3 Tegaserod Inhibited the Activity of the JAK Kinase Family

Figure 3:
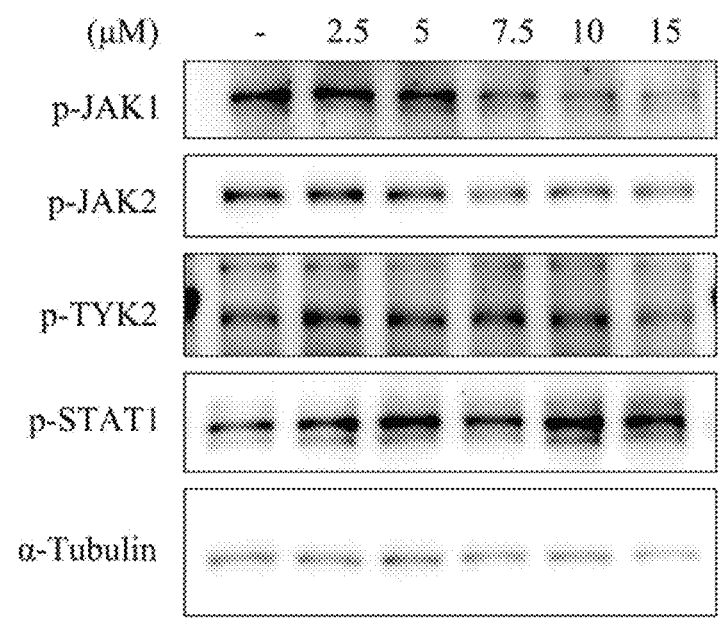
FIG. 3 is a schematic diagram of western blotting results illustrating that Tegaserod can selectively inhibit the phosphorylation of JAK kinases.

STAT3 is usually JAK-kinase-phosphorylated and activated by the autophosphorylated JAK kinase upstream thereof. Different concentrations of Tegaserod were added to DU145 cells, and after the cells were incubated for 2 h, it was found that Tegaserod at a concentration of 7.5 µM could inhibit the phosphorylation at JAK1 Tyr1022/1023 and JAK2 Tyr1007/1008 sites in DU145 cells, and Tegaserod at a high concentration (15 µM) could also inhibit the phosphorylation at a TYK2 Tyr1054/1055 site (FIG. 3). It indicated that Tegaserod was an inhibitor for the JAK kinase family, which showed a higher affinity to JAK1 and JAK2 than to TYK2. Tegaserod down-regulated the STAT3 phosphorylation in tumor cells by specifically inhibiting the activation of JAK kinase.

Example 4 Inhibitory Effect of Tegaserod on Tumor Cell Growth

Figure 4:
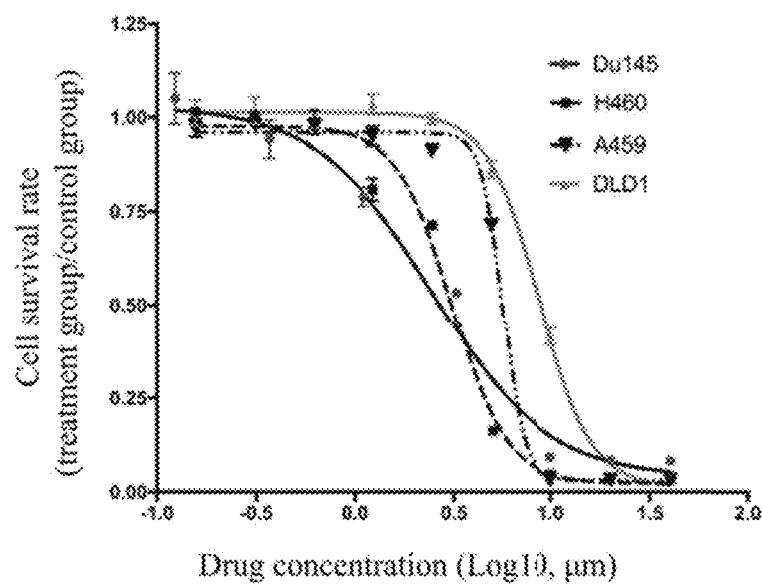
FIG. 4 is a schematic diagram illustrating the inhibition of Tegaserod on tumor cell growth in vitro.

Tegaserod had an inhibitory effect on the growth of tumor cells from many different sources (FIG. 4). After cells were treated with Tegaserod for 72 h, the cell viability was determined to reflect the inhibitory effect of the drug on cell growth. Growth inhibition $IC_{50}$ values of Tegaserod for various cells were as follows: prostate cancer DU145 cells: 2.5 µM; lung cancer H460 cells: 3.1 µM; lung cancer A549 cells: 5.7 µM, and DLD1 colon cancer cells: 8.7 µM.

Figure 5:
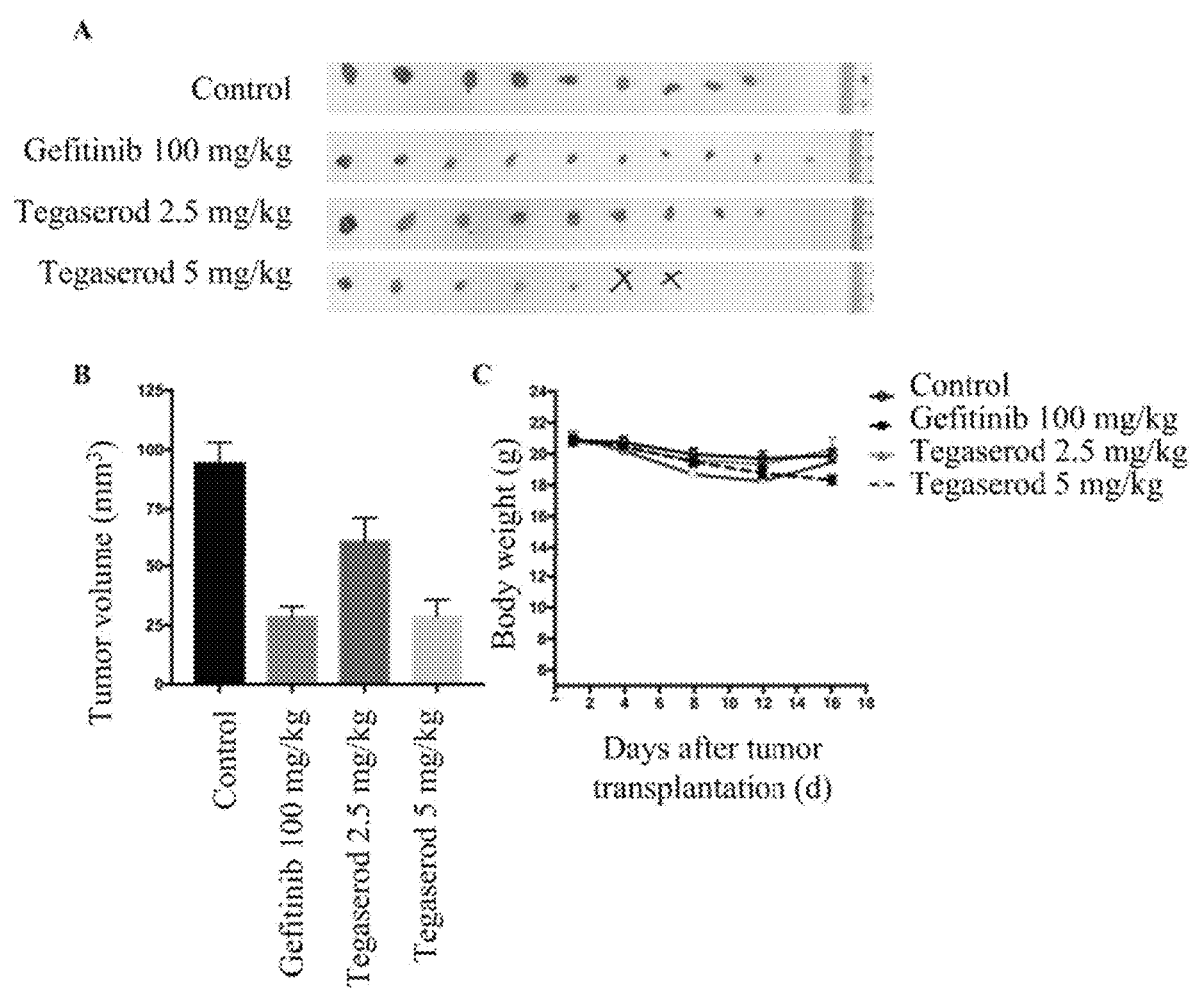
FIG. 5 is a schematic diagram illustrating that the intraperitoneal administration of Tegaserod can inhibit the growth of transplanted tumors in A549 nude mouse transplanted tumor models.

Example 5 Intraperitoneal Injection of Tegaserod Inhibited the Growth of Transplanted Tumors in Nude Mice In the nude mouse transplanted A549 lung cancer animal models, intraperitoneal injection of Tegaserod could inhibit the growth of transplanted tumor cells in the model animals (FIG. 5A and FIG. 5B). Compared with the control group, 5 mg/kg Tegaserod (i.p.) could effectively inhibit the growth of A549 tumor cells, with an anti-tumor effect comparable to that of 100 mg/kg gefitinib (p.o.). Throughout the experiment, body weights of all experimental mice did not change significantly (FIG. 5C), and at the experimental endpoint, no obvious organ damage was observed after anatomy, indicating that Tegaserod had no obvious toxicity and had high drug safety.

Figure 6:
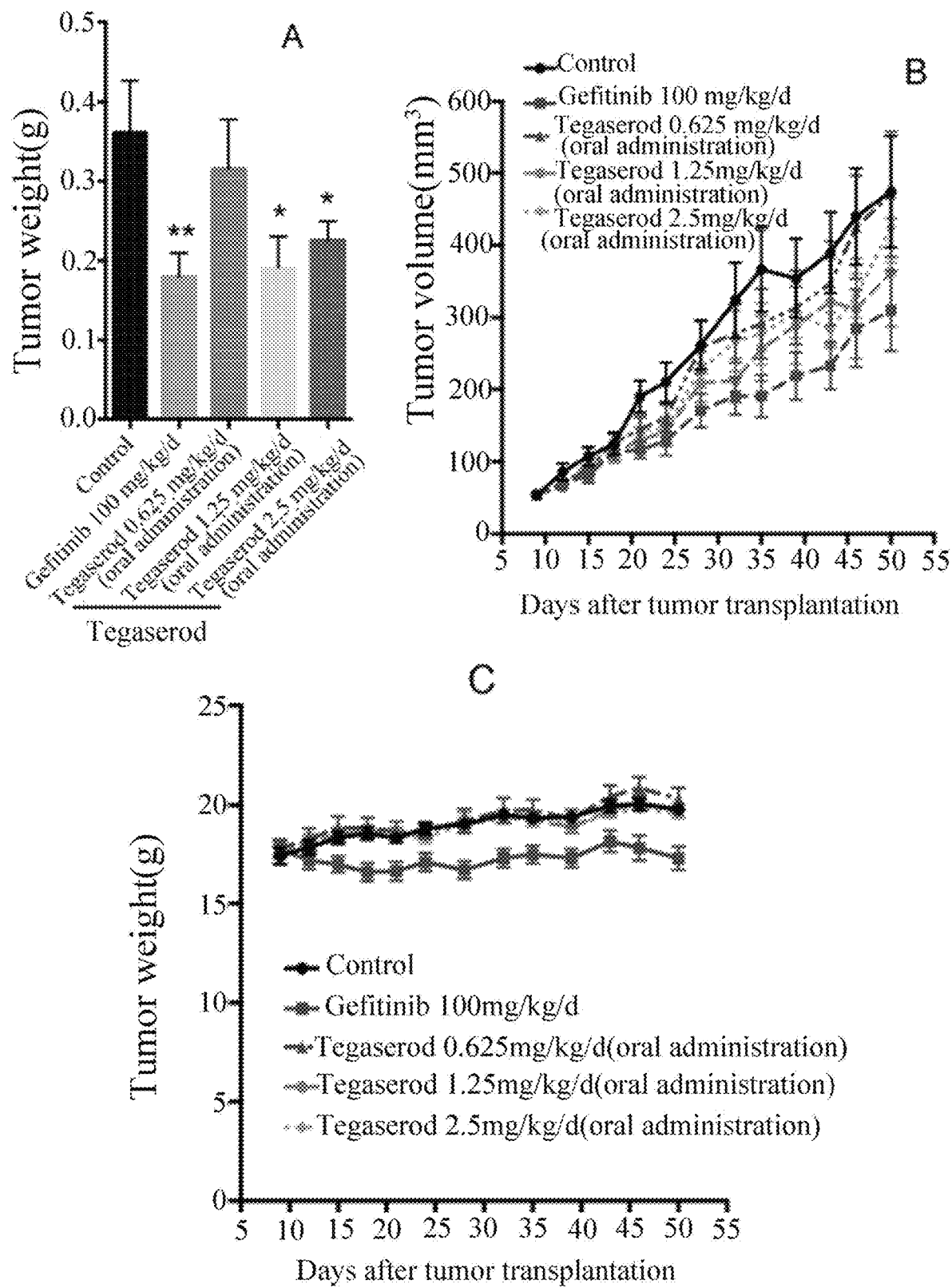
FIG. 6 shows that the oral administration of Tegaserod can effectively inhibit the growth of NSCLC A549 transplanted tumors in nude mice.

Example 6 Oral Administration of Tegaserod could Effectively Inhibit the Growth of NSCLC A549 Transplanted Tumors in Nude Mice Given that Tegaserod was administered orally in the treatment of IBS with constipation (IBS-C), it was tested whether oral administration of Tegaserod could effectively inhibit the growth of tumors in vivo. The tumor weight and tumor volume results in FIG. 6A and FIG. 6B showed that the oral administration of Tegaserod could inhibit the growth of A549 transplanted tumors in nude mice, and the data in FIG. 6C showed that the mice did not lose weight at the oral administration dosage, indicating that the dosage was safe and did not lead to obvious drug toxicity.

Figure 7:
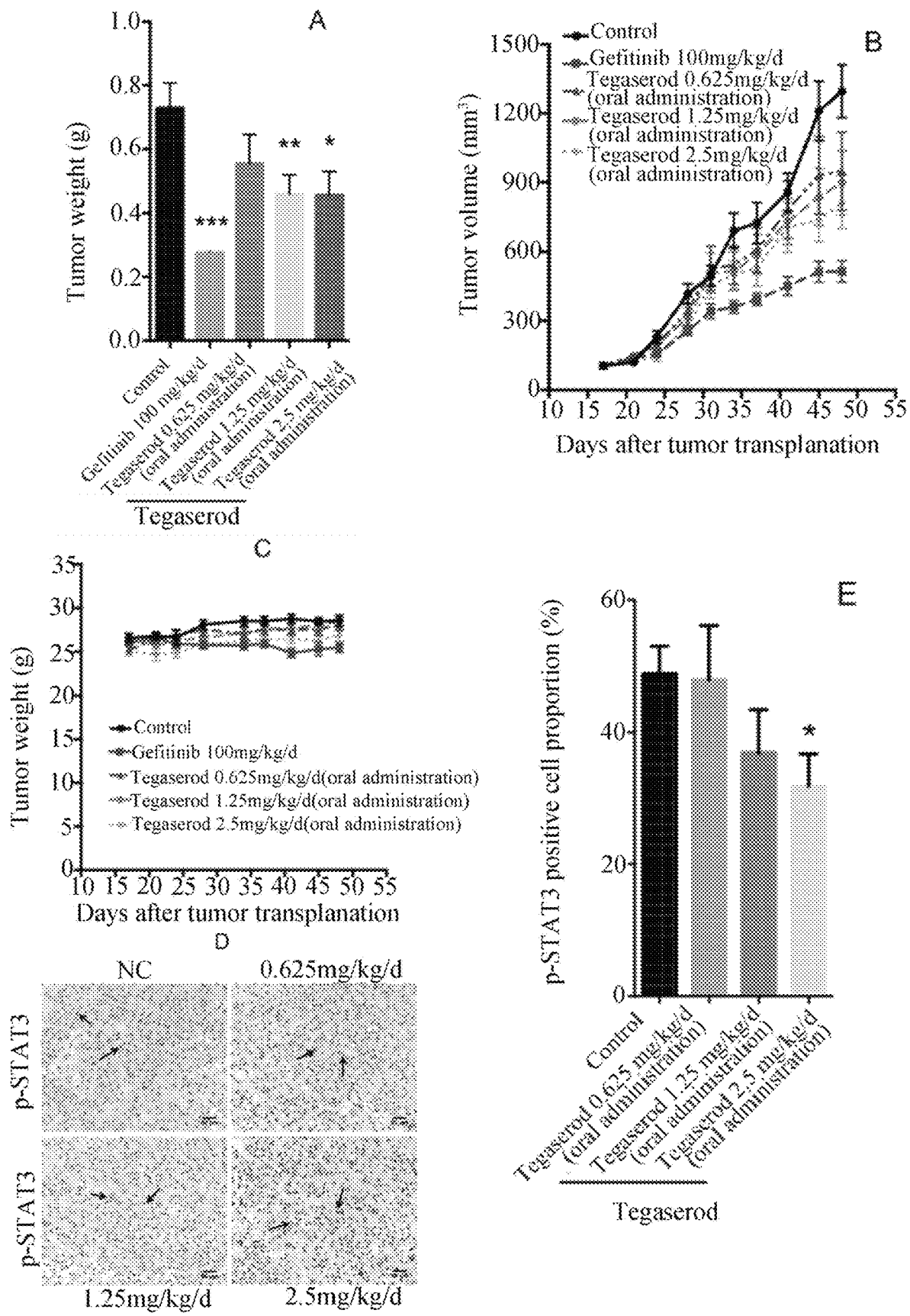
FIG. 7 shows that the oral administration of Tegaserod inhibits the growth of prostate cancer DU145 transplanted tumors in nude mice.

Example 7 Oral Administration of Tegaserod Inhibited the Growth of Prostate Cancer DU145 Transplanted Tumors in Nude Mice In addition, the human prostate cancer cell line DU145 with constitutive STAT3 activation was selected, and the effect of Tegaserod on the growth of transplanted tumors of the human prostate cancer cell line in nude mice was also tested. Results in FIG. 7A and FIG. 7B showed that the oral administration of Tegaserod could effectively inhibit the growth of DU145 transplanted tumors in nude mice, without obvious drug toxicity (FIG. 7C). The immunohistochemical results of phosphorylated STAT3 in FIG. 7D and FIG. 7E showed that Tegaserod could effectively inhibit the phosphorylation level of STAT3 in DU145 transplanted tumors in nude mice, and could target the JAK/STAT3 signaling pathway in vivo.

Figure 8:
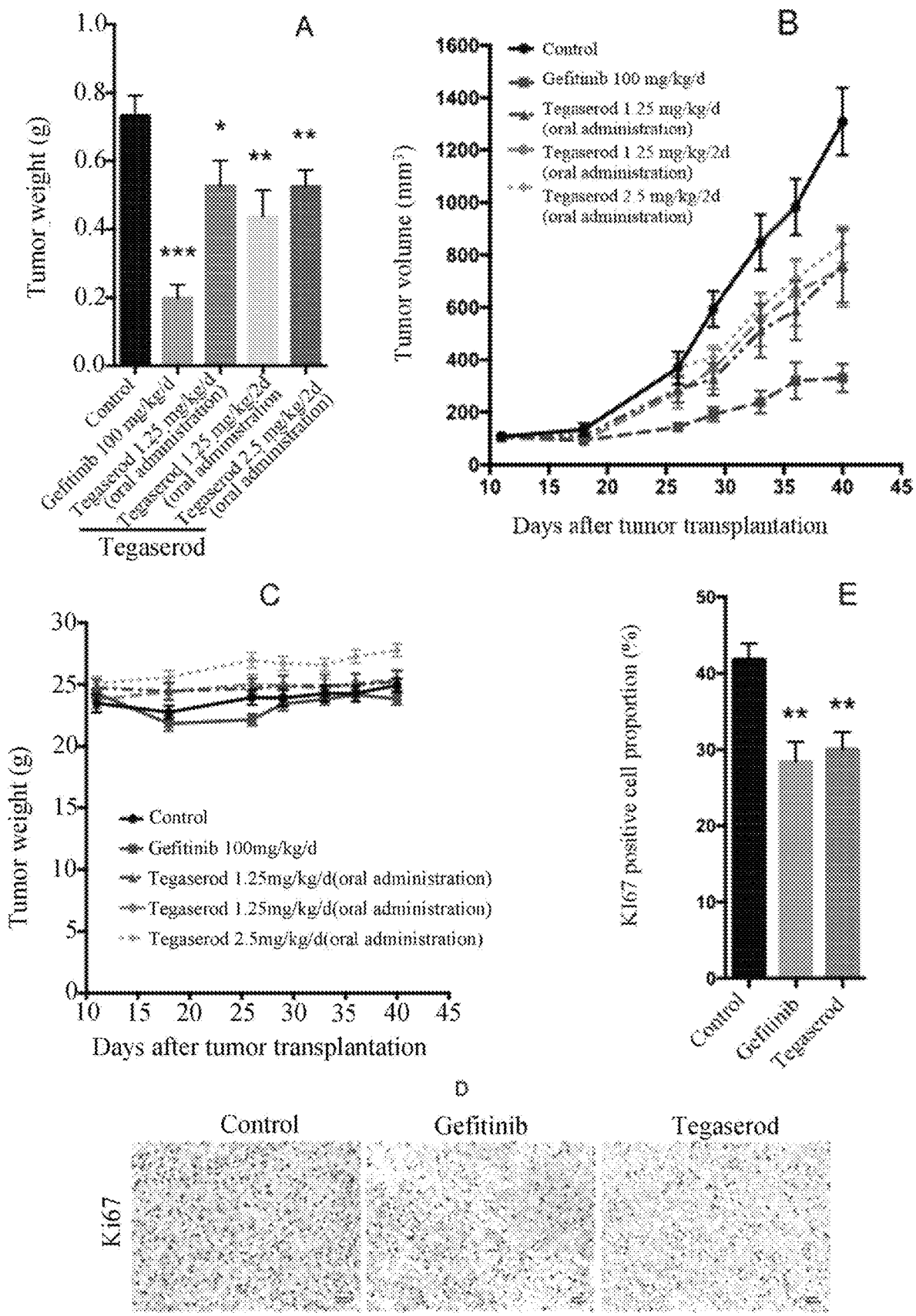
FIG. 8 shows that the low-dosage and low-frequency oral administration of Tegaserod can effectively inhibit the growth of DU145 transplanted tumors in nude mice.

Example 8 Low-Dosage and Low-Frequency Oral Administration of Tegaserod could Effectively Inhibit the Growth of DU145 Transplanted Tumors in Nude Mice In both A549 and DU145 transplanted tumor nude mouse models, it was observed that a tumor inhibition rate showed no dependence on a Tegaserod dosage, and high-dosage Tegaserod did not enhance the tumor inhibition activity. Then, different administration frequencies were tried to test whether the oral administration of Tegaserod could still effectively inhibit the tumor growth after the dosage frequency was further reduced in the high-dosage group. Results in both FIG. 8A and FIG. 8B showed that Tegaserod exhibited a stronger tumor inhibition ability when administered orally once every two days, and the body weight results of mice in FIG. 8C showed that Tegaserod exhibited no obvious drug toxicity when administered at the concentration and frequency. Immunohistochemical results of the cell proliferation marker Ki67 in FIG. 8D and FIG. 8E also showed that tumors exhibited a decreased proliferation ability after Tegaserod was orally administered at 1.25 mg/kg once every two days. The above results all showed that the low-dosage and low-frequency oral administration of Tegaserod could effectively inhibit the tumor growth.

Figure 9:
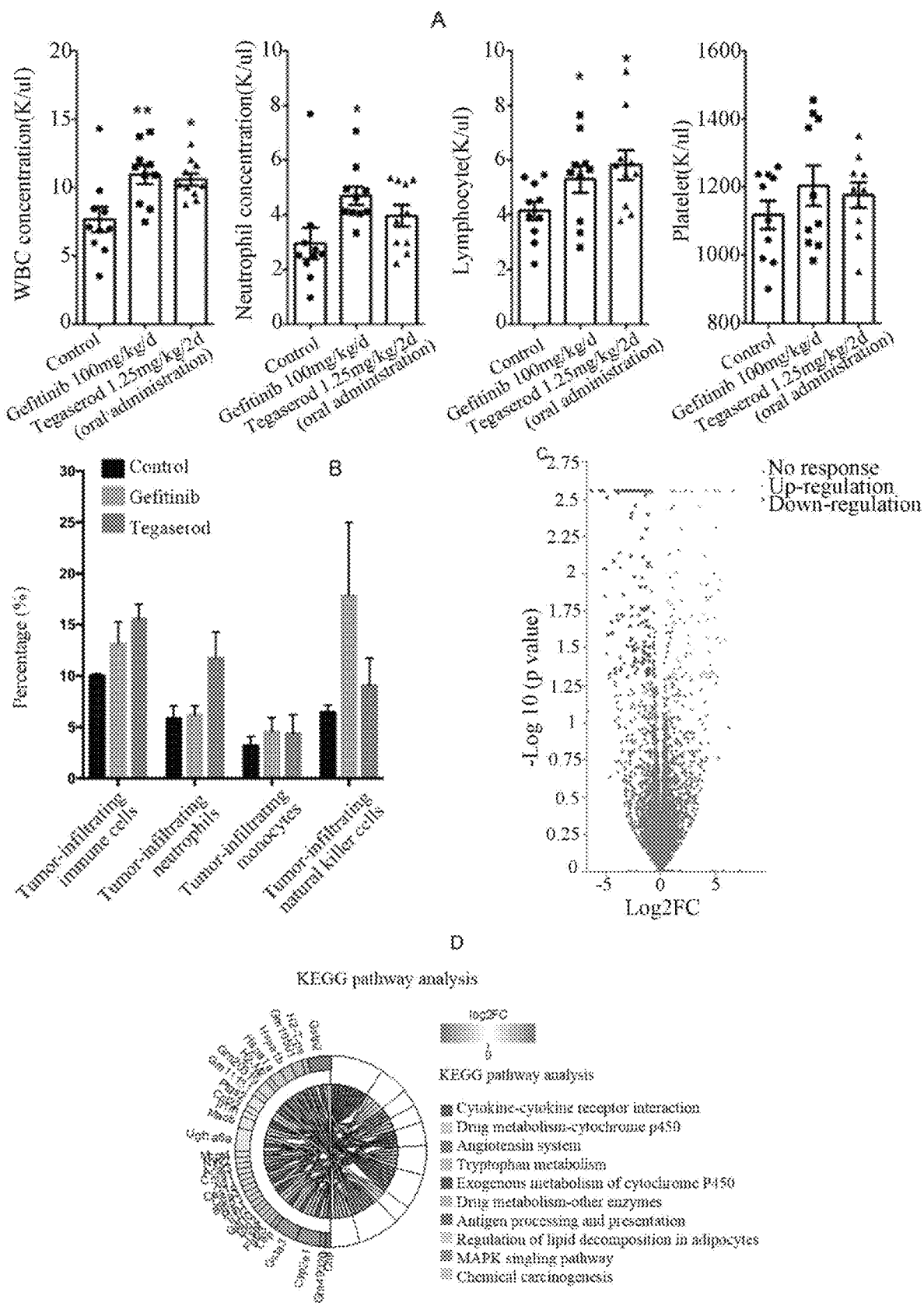
FIG. 9 shows that the oral administration of Tegaserod can activate a peripheral immune response and an immune response in TME.

Example 9 Oral Administration of Tegaserod could Activate a Peripheral Immune Response and an Immune Response in TME In view of the effectiveness of Tegaserod under low-dosage and low-frequency administration and the concentration-independent anti-tumor activity of Tegaserod, it was speculated that Tegaserod may be similar to an immunomodulator, which also modulated a tumor immune microenvironment (TIME) in vivo, thereby exhibiting dual-effect modulation to inhibit the tumor growth. In order to verify this hypothesis, the composition change of immune cells in peripheral blood after the administration of Tegaserod was first detected. The blood analysis data in FIG. 9A showed that, similar to the positive drug gefitinib, Tegaserod could stimulate the increase of total WBC count, neutrophils, lymphocytes, and platelets in the peripheral blood, thereby powerfully stimulating the peripheral immune response.

Furthermore, the composition and proportion of immune cells in DU145 transplanted tumors in nude mice were tested through FCM. Results in FIG. 9B showed that the administration of Tegaserod could increase the proportion of immune cells (CD45+) in tumors, namely, proportions of tumor-infiltrating inflammatory neutrophils (CD11b+Ly6G+), monocytes/macrophages (CD11b+Ly6C+), and natural killer cells (CD335+), thereby inhibiting the growth of tumor cells. The positive drug gefitinib also exhibited a similar immunomodulatory effect.

In order to further explore the immunomodulatory effect of Tegaserod in an anti-tumor process, the transcriptome sequencing technology was used to conduct mRNA sequencing for DU145 transplanted tumors in nude mice, and sequencing results were aligned to the mouse reference genome to obtain the overall mRNA expression of mouse-derived cells in DU145 transplanted tumors in nude mice. As shown in FIG. 9C, there were a large number of significantly changed genes in the mouse stromal cells of tumor samples in the Tegaserod treatment group, and the KEGG signaling pathway analysis (FIG. 9D) showed that genes involved in the cytokine-cytokine receptor interaction process and the antigen processing and presentation process were significantly up-regulated. This result is consistent with the FCM result in FIG. 9B, both of which prove that Tegaserod played an anti-tumor role by modulating TIME.

The above results indicated that Tegaserod could activate the composition and function of immune cells in the systemic environment and TME, thereby exerting double anti-tumor effects.

Figure 10:
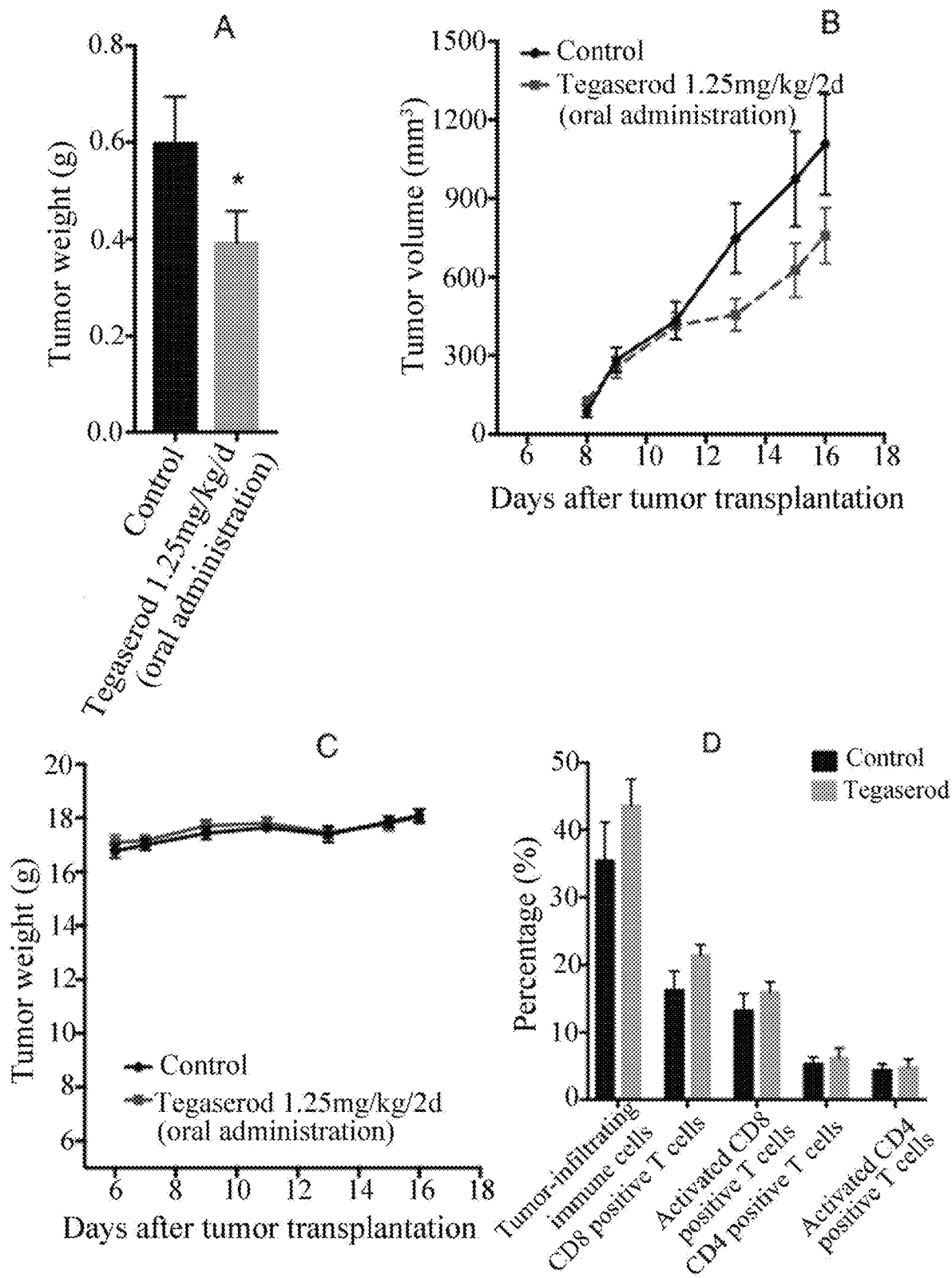
FIG. 10 shows that Tegaserod can activate the immune system to inhibit the growth of colorectal cancer (CRC) MC38 syngeneic tumors.

Example 10 Tegaserod could Activate the Immune System to Inhibit the Growth of CRC MC38 Syngeneic Tumors In the transplanted tumor nude mouse models, it was found that Tegaserod exhibited both the immune activation function and the anti-tumor effect. Some parts in nude mice had acquired immune cell deficiency and an imperfect immune system, and thus the anti-tumor effect and immunomodulatory effect of Tegaserod were further tested in immune-sound mice. Results showed that Tegaserod could effectively inhibit the growth of CRC MC38 transplanted tumors (FIG. 10A and FIG. 10B), without obvious drug toxicity (FIG. 10C). FCM results in FIG. 10D showed that Tegaserod promoted the infiltration of immune cells (CD45+) inside tumors. This result was consistent with the result for the DU145 transplanted tumor nude mouse model, both of which indicate the immune activation effect of Tegaserod. Moreover, in the Tegaserod groups, the infiltration of killer T cells (CD8+) and helper T cells (CD4+) within tumors was increased, and the proportion of activated T cells was also increased (CD4+CD69+ and CD8+CD69+) (FIG. 10D). These results indicated that Tegaserod could activate the tumor-killing effect of acquired immune cells to further exhibit the anti-tumor effect.

It should be understood that various changes and modifications can be made to the relevant conditions of the present disclosure by those skilled in the art after reading the above content of the present disclosure, and these equivalent forms also fall within the scope defined by the appended claims of the present disclosure.

What is claimed is:

1. A method for treating a tumor, comprising administering to a patient in need thereof an anti-tumor drug comprising Tegaserod or a pharmaceutically acceptable salt thereof, wherein a JAK-STAT3 signaling pathway in the tumor is abnormally activated and wherein the tumor is selected from the group consisting of cerebroma, gastric cancer, skin cancer, breast cancer, pancreatic cancer, prostate cancer, cervical cancer, and liver cancer.

2. The method according to claim 1, wherein abnormal activation of the JAK-STAT3 signaling pathway is manifested as an increased phosphorylation level of JAK1, JAK2, JAK3, Tyk2, or STAT3.

3. The method according to claim 2, wherein the increased phosphorylation level refers to an increased phosphorylation level at a site JAK1 Tyr1022/1023, JAK2 Tyr1007/1008, TYK2 Tyr1054/1055, or STAT3 Tyr705.

4. The method according to claim 1, wherein the pharmaceutically acceptable salt is Tegaserod maleate.

5. The method according to claim 1, wherein the tumor is selected from the group consisting of prostate cancer, and colon cancer.

6. The method according to claim 5, wherein the abnormal activation of the JAK-STAT3 signaling pathway is manifested as an increased phosphorylation level of JAK1, JAK2, JAK3, Tyk2, or STAT3.

7. The method according to claim 6, wherein the increased phosphorylation level refers to an increased phosphorylation level at a site JAK1 Tyr1022/1023, JAK2 Tyr1007/1008, TYK2 Tyr1054/1055, or STAT3 Tyr705.

8. The method according to claim 1, wherein the Tegaserod is administered in combination with an estrogen receptor modulator, an androgen receptor modulator, a retinoid receptor modulator, a cytotoxin/cytostatic agent, an antiproliferative agent, a protein transferase inhibitor, an HMG-COA reductase inhibitor, an HIV protein kinase inhibitor, a reverse transcriptase inhibitor, an angiogenesis inhibitor, a cell proliferation and survival signal inhibitor, a drug for interfering with cell cycle checkpoints, an apoptosis inducer, a cytotoxic drug, a tyrosine protein inhibitor, an EGFR inhibitor, a VEGFR inhibitor, a serine/threonine protein inhibitor, a Bcr-Abl inhibitor, a c-Kit inhibitor, a Met inhibitor, a Raf inhibitor, an MEK inhibitor, an MMP inhibitor, a topoisomerase inhibitor, a histone deacetylase inhibitor, a proteasome inhibitor, a CDK inhibitor, a Bcl-2 family protein inhibitor, a MDM2 family protein inhibitor, an IAP family protein inhibitor, an STAT family protein inhibitor, a PI3K inhibitor, an AKT inhibitor, an integrin blocker, interferon-α, interleukin-12, a COX-2 inhibitor, a p53 activator, a p53 activator, a VEGF antibody, an EGF antibody or a combination thereof.

9. The method according to claim 1, wherein the Tegaserod is administered in combination with aldesleukin, alendronic acid, alemtuzumab, alfaferone, alitretinoin, allopurinol, altretamine, aminoglutethimide, amifostine, amrubicin, amsacrine, anastrozole, aprepitant, arglabin, arsenic trioxide, aromasin, 5-azacytidine, azathioprine, Bacille Calmette-Guerin (BCG), bestatin, betamethasone acetate, betamethasone sodium phosphate, bexarotene, bicalutamide, bleomycin sulfate, bromouridine, bortezomib, busulfanum, calcitonin, capecitabine, carboplatin, carmustine, cefesone, celmoleukin, conjugated estrogens, daunorubicin, chlorambucil, cisplatin, cladribine, clodronate, cyclophosphamide, cytarabine, darbepoetin alfa, dacarbazine, actinomycin D, liposomal daunorubicin, dexamethasone, dexamethasone phosphate, estradiol valerate, denileukin diftitox 2, methylprednisolone, deslorelin, dexrazoxane, diethylstilbestrol, docetaxel, dolasetron, doxifluridine, doxorubicin, dronabinol, holmium-166-chitosan complex, epirubicin, epoetinalfa, eptaplatin, ergamisole, esterified estrogens, 17-α-estradiol, estramustine sodium phosphate, ethinyloestradiol, etidronic acid, etoposide, fadrozole, farstone, filgrastim, finasteride, fligrastim, floxuridine, fluconazole, fludarabine, 5-fluorodeoxyuridine monophosphate, 5-fluorouracil, fluoxymesterone, flutamide, formestane, fosteabine, fotemustine, fulvestrant, gamma globulin, gefitinib, gemcitabine, gemtuzumab, goserelin, granisetron hydrochloride, histrelin, hydrocortisone, erythro-hydroxynonyl adenine, hydroxyurea, ibritumomab tiuxetan, idarubicin, ifosfamide, imatinib, interferon-α, interferon-α 2, interferon α-2A, interferon α-2B, interferon α-n1, interferon α-n3, interferon β, interferon β-1a, interferon γ-1a, interleukin-2, irinotecan, lentinan sulfate, letrozole, leucovorin, leuprorelin, leuprorelin acetate, levotetramisole, levoleucovorin calcium, levothyroxine sodium, levothyroxine sodium preparation, liposome-encapsulated doxorubicin citrate, lomustine, lonidamine, mechlorethamine, methylcobalamin, medroxyprogesterone acetate, megestrol acetate, melphalan, 6-mercaptopurine, mesna, methotrexate, methyl aminolevulinate, miltefosine, minocycline, mitomycin C, mitotane, mitoxantrone, nedaplatin, nilutamide, NSC-631570, recombinant human interleukin 1-β, octreotide, ondansetron hydrochloride, oprelvekin, oxaliplatin, paclitaxel, palonosetron, pegaspargase, peginterferon alfa-2a, pegfilgrastim, pentostatin, picibanil, pilocarpine hydrochloride, pirarubicin, plicamycin, porfimer sodium, prednimustine, prednisolone, prednisolone steaglate, prednisolone sodium phosphate, prednisone, procarbazine, raltitrexed, rasburicase, rhenium-186 etidronate, rituximab, vitamin C, romurtide, sargramostim, semustine, sizofiran, sobuzoxane, methylprednisolone sodium succinate, sparfosic acid, stem cell therapy, streptozocin, strontium-89 chloride, levothyroxine sodium, tamoxifen, tamsulosin, tasonamin, tastolactone, recombinant human interleukin-2, temozolomide, teniposide, testosterone propionate, testride, thioguanine, thiotepa, thyrotropin, tiludronic acid, topotecan, toremifene, tositumomab, trastuzumab, treosulfan, tretinoin, trilostane, trimethylmelamine, trimetrexate, triptorelin acetate, triptorelin pamoate, UFT, uridine, valrubicin, vesnarinone, vinblastine, vincristine, vindesine, vinorelbine, virulizin, dexrazoxane, zinostatin stimalamer, ABI-007, acolbifene, interferon γ-1b, aprinocarsen, aminopterin, arzoxifene, asoprisnil, atamestane, atrasentan, BAY43-9006, bevacizumab, CCI-779, CDC-501, celecoxib, cetuximab, crisnatol, cyprottreone acetate, decitabine, DN-101, doxorubicin-MTC, dSLIM, dutasteride, edotecarin, eflornithine, exatecan, fenretinide, histamine dihydrochloride, histrelin hydrogel implant, holmium-166 DOTMP, ibandronic acid, interferon γ, peginterferon alfa-2b, ixabepilone, keyhole limpet hemocyanin, L-651582, lanreotide, lasofoxifene, chlordiazepoxide, clidinium, lonafarnib, miproxifene, minodronate, MS-209, liposomal MTP-PE, MX-6, nafarelin, nemorubicin, neovastat, nolatrexed, oblimersen, liposomal vincristine, osimertinib, polyglutamate paclitaxel, pamidronate disodium, PN-401, QS-21, quazepam, R-1549, raloxifene, ranpirnase, 13-cis retinoic acid, satraplatin, seocalcitol, T-138067, erlotinib, DHA-paclitaxel, thymosin α 1, tiazofurin, tipifarnib, tirapazamine, TLK-286, toremifene, trans-MID-lo7R, valspodar, vapreotide, vatalanib, verteporfin, vinflunine, Z-100, and zoledronic acid, or a combination thereof.

* * * * *